United States Patent [19]

Schmidhauser et al.

[11] Patent Number: 5,110,897

[45] Date of Patent: May 5, 1992

[54] THERMOPLASTIC POLYCARBONATE COMPOSITION HAVING IMPROVED OXYGEN BARRIER PROPERTIES FROM DIESTER DIOL

[75] Inventors: John C. Schmidhauser, Schenectady; Kathryn L. Longley, Saratoga Springs, both of N.Y.

[73] Assignee: General Electric Company, Schenectady, N.Y.

[21] Appl. No.: 520,905

[22] Filed: May 9, 1990

Related U.S. Application Data

[62] Division of Ser. No. 375,111, Jul. 3, 1989, abandoned.

[51] Int. Cl.$^5$ ............................................. C08G 63/64
[52] U.S. Cl. ..................................... 528/196; 528/125; 528/128; 528/171; 528/176; 528/193; 528/203
[58] Field of Search ............... 528/203, 125, 128, 176, 528/193, 171, 196

[56] References Cited

U.S. PATENT DOCUMENTS

| | | | |
|---|---|---|---|
| 2,999,835 | 9/1961 | Goldberg | 260/42 |
| 3,028,365 | 4/1962 | Schnell et al. | 260/47 |
| 3,334,154 | 8/1967 | Kim | 260/860 |
| 3,810,933 | 5/1974 | Banucci | 528/203 |
| 4,476,294 | 10/1984 | Mark | 528/125 |

FOREIGN PATENT DOCUMENTS 3523977  1/1986  Fed. Rep. of Germany.
61-16923 1/1986  Japan.

OTHER PUBLICATIONS

Chemical Abstracts, 61:8243–8244 (1964), Harsanyi et al.
Chemical Abstracts, 63: 17991c (1965), Ninagawa et al.
Chemical Abstracts, 65: 15278c (1966), Uno et al.
Chemical Abstracts, 66: 104837g (1967), Yoshimura et al.
Chemical Abstracts, 70: 69055j (1969), Kumano et al.
Chemical Abstracts, 77: 88003b (1972), Takars et al.
Chemical Abstracts, 81: 121641r (1974), Suda et al.
Chemical Abstracts, 98: 154902f (1983), Gilbert et al.

*Primary Examiner*—Harold D. Anderson
*Attorney, Agent, or Firm*—William H. Pittman; James C. Davis, Jr.

[57] ABSTRACT

High molecular weight, thermoplastic aromatic polycarbonate compositions exhibiting improved oxygen barrier properties are provided which comprise structural units derived from a diester bisphenol or a cyano-substituted bisphenol, or an aromatic dihydric phenol in admixture with either of the foregoing bisphenol compounds. Novel cyano-substituted bisphenol monomers are also provided.

16 Claims, No Drawings

THERMOPLASTIC POLYCARBONATE COMPOSITION HAVING IMPROVED OXYGEN BARRIER PROPERTIES FROM DIESTER DIOL

This application is a division of application Ser. No. 07/375,111, filed Jul. 3, 1989, now abandoned.

BACKGROUND OF THE INVENTION

This invention relates to thermoplastic aromatic polycarbonate compositions. More particularly, this invention relates to thermoplastic aromatic polycarbonate compositions having improved oxygen barrier properties.

Aromatic polycarbonates prepared from bisphenols are an important class of polymers known for having many attractive properties including high impact strength, optical clarity, toughness, good creep resistance, good dimensional stability, wide temperature limits and the like. This property profile allows the polymers to be used in a wide variety of applications. However, the polymers also possess a high permeability to gases which limits their usefulness in applications requiring good to moderate barrier properties particularly, for example, in form containers and food wraps used in the food and beverage industry for perishable products.

It would be desirable, therefore, to provide aromatic polycarbonates having improved oxygen barrier properties for use in such applications.

SUMMARY OF THE INVENTION

The present invention provides a thermoplastic aromatic polycarbonate resin having oxygen barrier properties which are superior to those of conventional polycarbonates, such as the bisphenol A-based polycarbonates, while retaining, to a substantial degree, most of the desirable physical and mechanical properties of the conventional polycarbonates.

The polycarbonate composition of this invention contains, (A) about 50 to about 100 mole percent of recurring structural units represented by the general formula $$\left(-O-\underset{}{\bigcirc}-\overset{O}{\underset{\|}{C}}-O-R_1-O-\overset{O}{\underset{\|}{C}}-\underset{}{\bigcirc}-O-\overset{O}{\underset{\|}{C}}-\right) \quad (I)$$

, or about 1 to about 100 mole percent of recurring structural units represented by the general formula $$\left(-O-\underset{(R_2)_m}{\bigcirc}-\underset{X}{\overset{C\equiv N}{|}}-\underset{(R_3)_n}{\bigcirc}-O-\overset{O}{\underset{\|}{C}}-\right) \quad (II)$$

mole percentages being based on total recurring structural units, and (B) recurring structural units represented by the general formula $$\left(-O-\underset{(R_4)_m}{\bigcirc}-(R_6)_k-\underset{(R_5)_n}{\bigcirc}-O-\overset{O}{\underset{\|}{C}}-\right) \quad (III)$$

wherein the polycarbonate composition comprising the structural units of Formula (I) further comprises about 0 to about 50 mole percent of the structural units of Formula (III) based on total recurring structural units, and the polycarbonate composition comprising the structural units of Formula (II) further comprises about 0 to about 99 mole percent of the structural units of Formula (III), and wherein $R_1$ is selected from divalent aliphatic hydrocarbon radicals, divalent aromatic radicals and divalent aliphatic ether radicals; $R_2$, $R_3$, $R_4$, and $R_5$ are independently monovalent hydrocarbon radicals and halogen radicals; $R_6$ is a divalent hydrocarbon radical or a $$-O-,\ -S-,\ -S-S-,\ -\overset{O}{\underset{\|}{C}}-,\ -\overset{O}{\underset{\|}{S}}-,\ \text{or}\ -\overset{O}{\underset{\underset{\|}{O}}{\overset{\|}{S}}}-$$

radical; X is a trivalent hydrocarbon radical; m and n are independently numbers in the range of 0 to about 4, and k is 0 or 1.

The present invention is also directed to novel cyano-substituted bisphenol monomers of the general formula $$HO-\underset{(R_2)_m}{\bigcirc}-\underset{X}{\overset{C\equiv N}{|}}-\underset{(R_3)_n}{\bigcirc}-OH$$

wherein $R_2$, $R_3$, X, m and n are as defined above. These monomers are useful in preparing the polycarbonate composition of Formula (II) and impart to those polycarbonates improved barriers to oxygen permeability.

DETAILED DESCRIPTION OF THE INVENTION

The present invention is directed to polycarbonate resins having improved oxygen barrier properties.

In preferred embodiments $R_1$ is a divalent alkylene, cycloalkylene, divalent alkylene ether, or a cycloalkylene ether group. The preferred alkylene groups are those containing about 1 to about 20 carbon atoms, and can be straight chain or branched alkylene groups. The preferred cycloalkylene radicals contain about 4 to about 7 ring carbon atoms. Most preferably, $R_1$ is a straight chain divalent ethylene group, i.e., —CH$_2$—CH$_2$—, or a straight chain divalent butylene group, i.e., —CH$_2$—CH$_2$—CH$_2$—CH$_2$—.

The divalent aliphatic ether groups represented by $R_1$ have the general formula —(R'—O)$_p$—R"— wherein R' and R" are independently alkylene or cycloalkylene groups, and p is a positive number having an average value of about 1 to about 10. Preferred alkylene groups represented by R' and R" are those containing about 1 to about 20 carbon atoms, and may be branched or straight chain alkylene groups. Preferred cycloalkylene groups represented by R' and R" are those containing about 4 to about 7 ring carbon atoms. Preferably, R' and R" are both straight chain ethylene groups and p is 1.

In preferred embodiments of Formula (II) m and n are 0 or 1, and $R_2$ and $R_3$ are independently monovalent aliphatic radicals, preferably alkyl and cycloalkyl radicals. The preferred alkyl radicals are those containing from 1 to 10 carbon atoms. Examples of preferred alkyl radicals include methyl, ethyl, propyl, isopropyl, butyl, tertiary butyl, pentyl and neopentyl with methyl being most preferred. The preferred cycloalkyl radicals are those containing from about 4 to about 7 ring carbon atoms. Examples of preferred cycloalkyl radicals include cyclobutyl, cyclopentyl, cyclohexyl, methylcyclohexyl, and cycloheptyl. When more than one $R_2$ and $R_3$ substituent are present, they may be the same or different. Preferably, $R_2$ and $R_3$ are both methyl groups and most preferably methyl groups in the 3,3' positions of the aromatic rings with respect to X.

X preferably represents aliphatic trivalent radicals containing 1 to about 6 carbon atoms. Most preferably, X is an aliphatic trivalent radical containing 5 carbon atoms or an aliphatic trivalent radical containing 6 carbon atoms.

In general, the aromatic rings in Formula (II) are bonded to the same carbon atom in the carbon chain represented by X and the cyano group is bonded to one of the end carbons of X.

Preferred embodiments of the structural units of Formula (II) include those of the following structures:

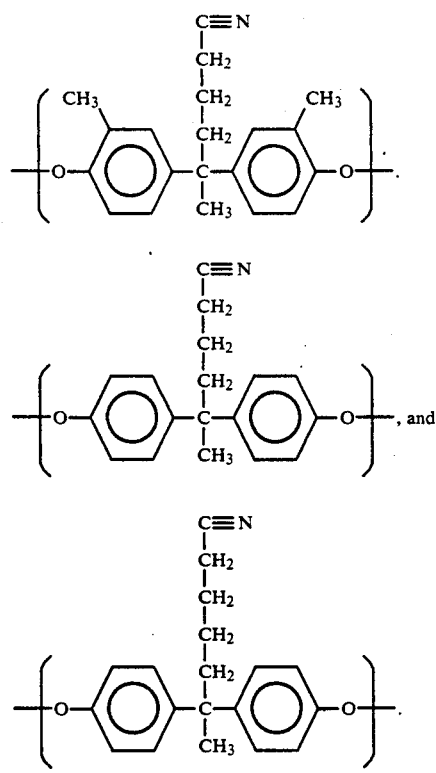

In preferred embodiments of Formula (III) m and n are 0 or 1, $R_4$ and $R_5$ are independently monovalent hydrocarbon groups such as alkyl, cycloalkyl, aryl, arylalkyl, and alkylaryl groups. The preferred alkyl groups are those containing from 1 to about 10 carbon atoms, for example, methyl, ethyl, propyl, isopropyl, butyl, tertiary butyl, pentyl and neopentyl, with methyl being most preferred. The preferred cycloalkyl groups are those containing from 4 to about 7 ring carbon atoms, for example, cyclobutyl, cyclopentyl, cyclohexyl, methylcyclohexyl and cycloheptyl. The preferred aryl radicals are those containing from 6 to 12 ring carbon atoms, for example, phenyl, biphenyl and naphthyl. The preferred arylalkyl and alkylaryl groups are those containing about 7 to about 14 carbon atoms. When more than one $R_4$ or $R_5$ substituent are present on the aromatic ring, they may be the same or different. Preferably, $R_4$ and $R_5$ are independently both methyl groups and most preferably, are both methyl groups in the 3,3' positions of the aromatic rings with respect to $R_6$.

$R_6$ preferably represents divalent hydrocarbon groups such as the alkylene, cycloalkylene, alkylidene and cycloalkylidene groups. Preferred alkylene and alkylidene groups are those containing about 1 to about 10 carbon atoms. Preferred cycloalkylene and cycloalkylidene groups are those containing about 4 to about 7 ring carbon atoms. When k is 0, the aromatic nuclear residues are directly joined without any intervening alkylene or other bridging group. Preferably, $R_6$ is an isopropylidene group.

The polycarbonate composition of this invention contain an oxygen-barrier improving amount of the structural units of either Formula (I) or Formula (II). An oxygen-barrier improving amount is defined herein as that amount sufficient to provide an oxygen barrier greater than that afforded by bisphenol A polycarbonate. The polycarbonate composition containing the structural units of Formula (I) contains about 50 to about 100 mole percent, and preferably about 65 to about 100 mole percent, of the structural units of Formula (I), and about 0 to about 50 mole percent of the structural units of Formula (III). The polycarbonate composition containing the structural units of Formula (II) contains about 1 to about 100 mole percent, and preferably about 50 to about 100 mole percent, of the structural units of Formula (II) and about 0 to about 99 mole percent and preferably about 0 to about 50 mole percent, of the structural units of Formula (III).

The units represented by Formula (I) are derived from diester bisphenol compounds having the general formula

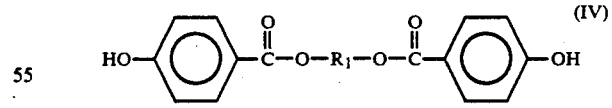

wherein $R_1$ is as defined above.

Specific examples of diester bisphenol compounds useful herein include 4,4'-[2,2'-oxybis(ethylene-1-oxycarbonyl)]diphenol, 4,4'-(1,4-bisoxycarbonylbutylene)diphenol and 4,4'-(1,2-bisoxycarbonylethylene)diphenol.

The diester bisphenol compounds of formula (IV) can be conveniently prepared from the reaction of p-acetoxybenzoyl chloride with the corresponding dihydroxy aliphatic compound or dihydroxy aliphatic ether compound to esterify the diol, followed by hydrolysis to yield the analogous diester bisphenol of Formula (IV) according to the following scheme:

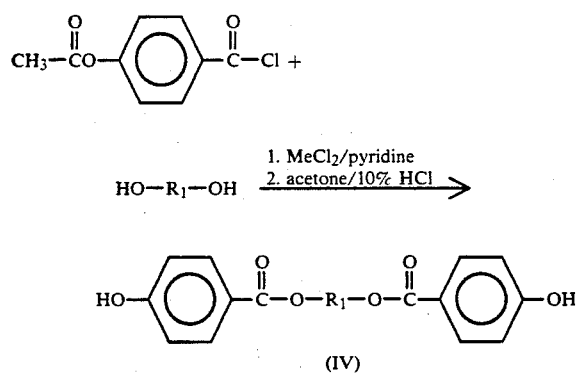

(IV)

Suitable diester bisphenol compounds for use herein and their preparation are also described in detail in U.S. Pat. No. 4,476,294, which is incorporated herein by reference.

The units represented by Formula (II) are derived from novel cyano-substituted bisphenol compounds having the general formula,

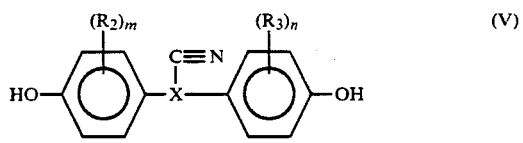

(V)

wherein $R_2$, $R_3$, X, m and n are as defined above.

Specific examples of suitable cyano-substituted bisphenols include 5,5-bis(4-hydroxyphenyl)hexanenitrile, 4,4-bis(4-hydroxyphenyl)pentanenitrile, and 4,4-bis(4-hydroxy-3-methylphenyl)pentanenitrile.

The cyano-substituted bisphenol compounds of Formula (V) can be prepared by any of several suitable methods. In one method, such compounds are prepared by the acid catalyzed condensation reaction of a cyano-substituted ketone with the corresponding substituted phenol to produce a cyano-bisphenol. As an example of this method, 5-oxohexanenitrile is condensed with phenol to give 5,5-bis(4-hydroxyphenyl)hexanenitrile according to the reaction scheme:

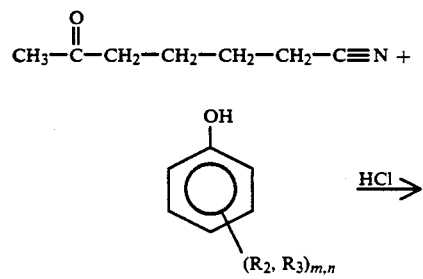

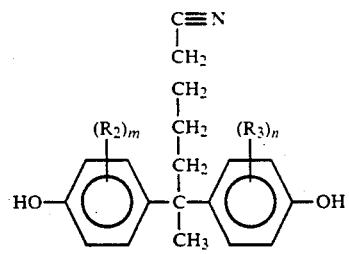

It is important that anhydrous conditions are maintained in this method since the presence of water can lead to hydrolysis of the cyano group which results in an unwanted mixture of phenyl ester-containing products. As shown, the reaction of different substituted phenols with different substituted ketones will yield a wide variety of analogous reaction products.

In another method for preparing cyanobisphenol compounds, an ester-functionalized bisphenol is prepared and then reacted with aqueous ammonium hydroxide to give the analogous amide, followed by refluxing with acetic anhydride to yield the diacetate which then undergoes hydrolysis to provide the cyano-substituted bisphenol represented by Formula (V) above. For example, ethyl 4,4-bis(4-hydroxyphenyl)-pentanoate is converted to the corresponding amide and nitrile bisphenol according to the following scheme:

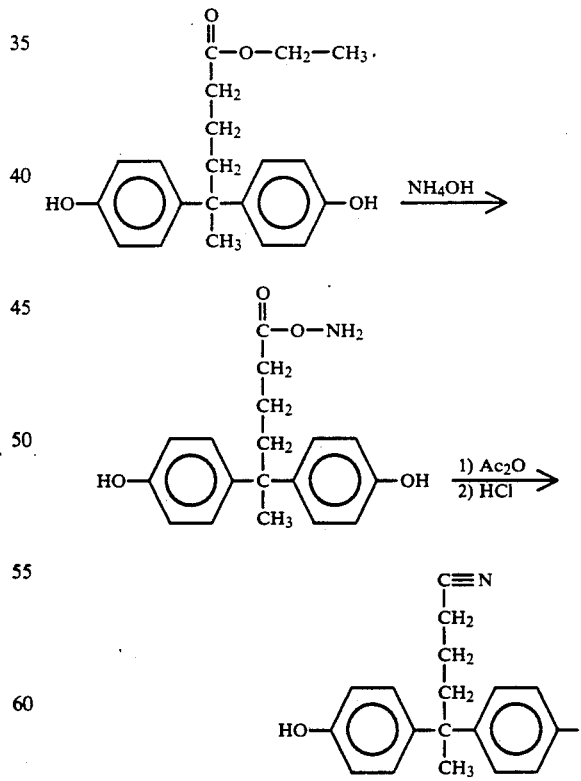

As another example of this method, the same sequence of reactions was also used to convert ethyl 4,4-bis(4-hydroxy-3-methylphenyl)pentanoate to the corresponding amide and nitrile according to the scheme:

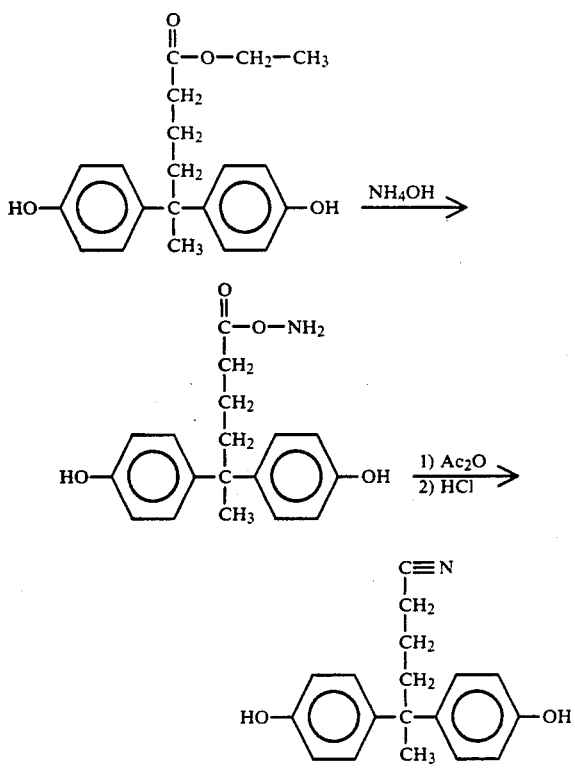

This method is suitable for preparing a broad range of cyano-functionalized bisphenols from the corresponding esters.

The units represented by Formula (III) are derived from dihydric phenols well known for use in preparing aromatic polycarbonates and polyarylates. Suitable dihydric phenols can be represented by the general formula

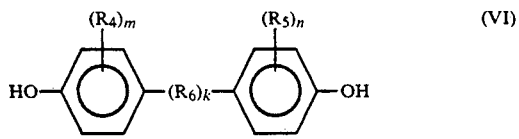

wherein $R_4$, $R_5$, $R_6$, m, n and k are as defined above.

Examples of suitable dihydric phenols and methods for preparing them are disclosed, for example, in U.S. Pat. Nos. 2,999,835, 3,028,365 and 3,334,154, which are each incorporated by reference herein. Particularly useful and preferred dihydric phenols are 2,2-bis(4-hydroxyphenyl)propane (i.e. bisphenol A) and 2,2-bis(4-hydroxy-3-methylphenyl)propane.

The polycarbonate resin compositions of the present invention are prepared by reacting the diester bisphenol of Formula (IV) or the cyano-substituted bisphenol of Formula (V) with a carbonate precursor under reaction conditions effective to form high molecular weight polycarbonates containing the structural units of Formulas (I) or (II).

In the event a carbonate copolymer rather than a homopolymer is desired, either a diester bisphenol of Formula (IV), or a cyano-substituted bisphenol of Formula (V), in admixture with a bisphenol-type dihydric phenol of Formula (VI), can be reacted with a carbonate precursor under the appropriate reaction conditions effective to form high molecular weight polycarbonates containing the structural units of Formulas (I) and (III) or of Formulas (II) and (III), respectively. It is also contemplated in the practice of this invention to employ two or more different dihydric phenols such as described above or a copolymer of a dihydric phenol with a glycol or with a hydroxy or acid-terminated polyester, or with a dibasic acid.

The heterogeneous interfacial polymerization process typically used in preparing conventional polycarbonates cannot be used to prepare the high molecular weight polycarbonates derived from the diester bisphenols used in this invention because the presence in such a method of high amounts of diester bisphenols such as those amounts used herein has been found to lead to the formation of low molecular polycarbonates, which is undesirable for purposes of the present invention because such low molecular weight polymers tend to be brittle and unable to form ductile films. While not wishing to be bound by any theory, it is believed that such low molecular weight polymers are formed in such a process as a result of the insolubility of the monomers and oligomers in the solvent.

Other methods conventionally used to prepare polycarbonates, for example, a solution method, may be used to prepare the diester bisphenol-containing polycarbonates of this invention.

In one method for preparing the polycarbonates from diester bisphenols, a reaction mixture is prepared containing the diester bisphenol dissolved in an organic solvent such as methylene chloride, a miscible organic acid acceptor such as pyridine, the dihydric phenol (if desired), and a molecular weight regulator. The carbonate precursor, such as a carbonyl halide, for example, phosgene, is then added to the mixture.

The reaction temperature may vary from below 0° C. to about 100° C. The reaction proceeds satisfactorily at temperatures from about room temperature (25° C.) to about 50° C.

Conventional methods, including the heterogeneous interfacial process, can be used to prepare the polycarbonates of this invention from the cyano-substituted bisphenol monomers. In the interfacial method, two immiscible solvent systems are used for the reactants, one being an aqueous solvent system and the other being a water immiscible organic solvent system such as methylene chloride. The dihydric phenol (if desired) is dissolved in the aqueous system, such as an alkaline aqueous system, while the cyano-substituted bisphenol is dissolved in the organic solvent system. The addition of the carbonate precursor, such as a carbonyl halide such as phosgene, is carried out under basic conditions by using an aqueous caustic solution to maintain the pH in the basic range. Also present in the reaction mixture are a catalyst and a molecular weight regulator.

As in the preparation of the polycarbonate from dihydric bisphenol, the reaction temperature of the process using the cyano-substituted bisphenol can vary from below 0° C. to above 100° C., but is preferably in the range of about room temperature to about 50° C.

In accordance with the present invention, the amount of the diester bisphenol or cyano-substituted bisphenol used is an amount effective to improve the oxygen barrier properties of the polycarbonate resin, but insufficient to significantly affect, in a deleteriously manner, the other advantageous properties of the aromatic polycarbonate resin.

The carbonate precursor useful in preparing the polycarbonates of this invention can be either a carbonyl halide, a carbonate ester, or a haloformate. Suitable carbonyl halides include carbonyl chloride (phosgene), carbonyl bromide and mixtures thereof. Typical of the carbonate esters which can be used herein are diphenyl carbonate; di-(halophenyl)carbonates, such as di-(chlorophenyl)carbonate, di-(bromophenyl)carbonate, di-(trichlorophenyl)carbonate, di-(tribromophenyl)carbonate, and the like; di-(alkylphenyl)carbonate, such as di-(tolyl)carbonate and the like; di-(naphthyl)carbonate; di-(chloronaphthyl)carbonate; phenyl tolyl carbonate; chlorophenyl chloronaphthyl carbonate; and the like, or mixtures thereof. The haloformates suitable for use herein include bishaloformates of dihydric phenols (e.g., bischloroformates of hydroquinone), or glycols (e.g., bishaloformates of ethylene glycol, neopentyl glycol, polyethylene glycol), and the like. The preferred carbonate precursor for use herein is phosgene.

In the preparation of the polycarbonates, an amount of carbonate precursor which is at least equal to the amounts of diester bisphenol or cyano-substituted bisphenol or mixtures of either with bisphenol-type dihydric phenol(s) is preferably used. Generally, an excess of carbonate precursor is most preferably used.

A molecular weight regulator, and a catalyst are preferably used in preparing the polycarbonates of this invention.

Molecular weight regulators which can be used herein include monohydric phenols or their derivatives, such as phenol, p-phenylphenol, paratertiarybutylphenol, parabromophenol, and the like; primary and secondary amines; and monofunctional carboxylic acids or their derivatives, such as the aryl ester of benzoic acid. The preferred molecular weight regulator for use herein is phenol.

Catalysts useful herein can be any catalyst which can accelerate or promote or otherwise aid the polymerization of bisphenol A with phosgene. Suitable catalysts include tertiary amines, such as trimethylamine, triethylamine, tripropylamine, diethylpropylamine, tributylamine, and the like; alkylaryl amines such as N,N-dimethylaniline, N,N-diethylaniline, N,N-dimethylnaphthylamine, benzyldimethylamine, alpha-methylbenzyldimethylamine; heterocyclic amines, such as pyridine and 4-dimethylaminopyridine; quaternary ammonium compounds, such as, for example, tetraethylammonium bromide, cetyl triethyl ammonium bromide, tetra-n-heptyl-ammonium iodide, tetra-n-propyl ammonium bromide, tetramethylammonium chloride, tetramethyl ammonium hydroxide, tetra-n-butylammonium iodide, benzyltrimethylammonium chloride, trioctylammonium chloride, and quaternary phosphonium compounds, such as, n-butyltriphenyl phosphonium bromide and methyltriphenyl phosphonium bromide. The preferred catalyst for purposes of this invention is triethylamine.

Generally, the amount of catalyst is in the range of about 0.05 to about 10.0 mole percent, and preferably in the range of about 0.8 to about 2.0 mole percent, based on the amount of bisphenol present.

The polycarbonates and copolycarbonates of the present invention generally have a weight average molecular weight in the range of from about 10,000 to about 300,000, and preferably from about 25,000 to about 100,000, as determined by gel permeation chromatography.

The polycarbonates and copolycarbonates of the present invention can be admixed, if desired, with any of the commonly known additives and fillers, such as glass, talc, mica and clay; impact modifiers, ultraviolet radiation absorbers, e.g., benzophenones and the benzotriazoles; color stabilizers and flame retardants.

The present invention is also directed to the novel cyano-substituted bisphenol monomers of Formula (V).

These monomers can be prepared according to methods previously discussed herein. In general, the most useful cyano-substituted monomers for providing polycarbonates with improved oxygen barrier properties are those having the following formulas:

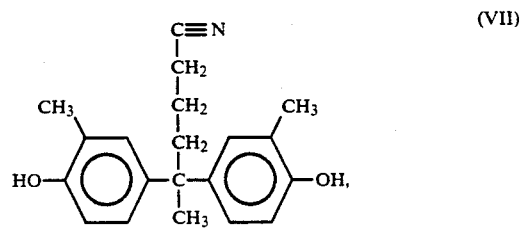

(VII)

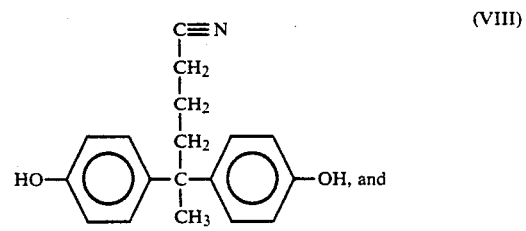

(VIII)

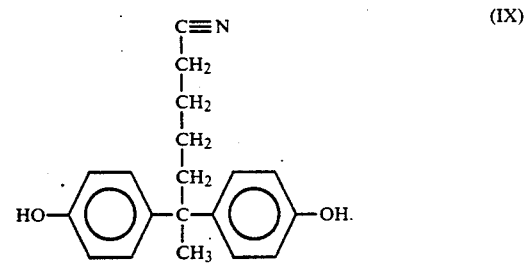

(IX)

Formulas (VII), (VIII), and (IX) represent 4,4-bis(4-hydroxy-3-methyl)pentanenitrile, 4,4-bis(4-hydroxyphenyl)pentanenitrile, and 5,5-bis(4-hydroxyphenyl)hexanenitrile, respectively.

The invention is illustrated without limitation in the following examples.

Examples 1–3 illustrate the preparation of three diester bisphenols which are useful in preparing the polycarbonates of the present invention. The characterization data for each bisphenol is listed in Table I.

EXAMPLE 1

Preparation of 4,4-[2,2'-oxybis([ethylene-1-oxycarbonyl)]diphenol

Pyridine (150 milliliters) was added to a solution of p-acetoxybenzoyl chloride (79.4 grams, 0.4 moles), 2-hydroxyethylether (21.2 grams, 0.2 mole) and methylene chloride (450 milliliters) over 0.5 hours. After being stirred at ambient temperature for 2 hours, the solution was washed first with a 10% HCl solution and then with water. The solution was dried over magnesium sulfate and the solvent removed from the solution in vacuo to provide a crude beige-white solid product (72.55 grams, 84% yield). Recrystallization of the crude product from methanol yielded the diacetate of bisphenol as small white needles (54.84 grams, 64% yield). A solution of the diacetate of bisphenol (54.4 grams, 0.128 mole), acetone (600 milliliters), and 10% HCl solution (200 milliliters) was then refluxed for 5 hours, and water and ethyl acetate added to the cooled solution until two phases were separated. The water layer was extracted with additional ethylacetate. The combined organic fractions were washed with saturated sodium bicarbonate solution and water, dried over magnesium sulfate, and concentrated by rotary evaporation to give 4,4'-[2,2'-oxybis(ethylene-1-oxycarbonyl)]diphenol, as a white solid (36.26 grams, 69.2% of theory).

EXAMPLE 2

Preparation of 4,4'-(1,4-bisoxycarbonylbutylene)diphenol

The procedure set forth in Example 1 was repeated except that 1,4-butanediol was substituted for 2-hydroxyethylether to obtain the diester bisphenol product, 4,4'-(1,4-bisoxycarbonylbutylene)diphenol.

EXAMPLE 3

Preparation of 4,4'-(1,2-bisoxycarbonylethylene)diphenol

The procedure recited in Example 1 was repeated except that 1,2-ethanediol was substituted for 2-hydroxyethylether to obtain the diester bisphenol product, 4,4'-(1,2-bisoxycarbonylethylene)diphenol.

TABLE I

Characterization of Diester Bisphenols Prepared in Examples 1–3

Example 1: 4,4'-[2,2'-Oxybis(ethylene-1-oxycarbonyl)]-diphenol

Melting Point: 136.0°–137.0° C.

$^1$H NMR: $\delta$7.92 (d, 4H, J=8 Hz), 6.89 (d, 4H, J=8 Hz), 4.42 (t, 4H, J=5 Hz), 3.89 (t, 4H, J=5 Hz).

$^{13}$C NMR: $\delta$166.5, 162.6, 132.5, 122.5, 116.0, 69.7, 64.3

Example 2: 4,4'-(1,4-bisoxycarbonylbutylene)diphenol

Melting Point: 180.0°–183.0° C.

$^1$H NMR: $\delta$7.81 (d, 4H, J=8.8 Hz), 6.84, (d, 4H, J=8.8 Hz), 4.26 (s, 4H), 1.82 (s, 4H).

$^{13}$C NMR: $\delta$165.6, 161.8, 131,4, 120.5, 115.3, 63.7, 25.1

Example 3: 4.4'-(1,2-bisoxycarbonylethylene)diphenol

Melting Point: 242.0°–244.0° C.

$^1$H NMR: $\delta$7.81 (d, 4H, J=8.7 Hz), 6.84 (d, 4H, J=8.8 Hz), 4,54 (s, 4H).

$^{13}$C NMR: $\delta$165.4, 162.1, 131.5, 120.1, 115.4, 62.4

Examples 4–12 illustrate the preparation of polycarbonates and copolycarbonates from the diester bisphenol monomers prepared in Examples 1–3, wherein the mole percent of monomer is varied from 50 to 100%, based on total moles of bisphenol monomers present. Comparative Example 13 illustrates the preparation of polycarbonate from bisphenol A alone. Characterization data and oxygen permeability measurements for the polycarbonates prepared in Examples 4–13 are provided in Table II.

EXAMPLES 4–6

Preparation of Polycarbonate from 4,4'[2,2-oxybis(ethylene-1-oxycarbonyl)]diphenol A suitably sized flask was charged with bisphenol A (except in Example 4, wherein only the diester bisphenol was used) and 4,4'-[2,2'-oxybis(ethylene-1-oxycarbonyl)]diphenol, as prepared in Example 1 above, in varying molar proportions as indicated below in Table II such that there was a total of 0.062 mole bisphenol, methylene chloride (90 milliliters), pyridine (30 milliliters), and 5 weight/volume percent phenol/methylene chloride solution (2.9 milliliters, 2.5 mole percent). Phosgene gas was then bubbled through the solution for about 20 minutes (flow rate= 0.4 grams/minute). At the end of the reaction, nitrogen was bubbled through to purge excess unreacted phosgene. The polymer solution was then precipitated into methanol (about 500 milliliters), filtered and redissolved into methylene chloride. This solution was then washed with dilute HCl solution and further washed repeatedly with water, and again precipitated into methanol. Filtering and drying in vacuo gave the copolycarbonate product as an off-white powder.

EXAMPLES 7–9

Preparation of Polycarbonate From 4,4'-(1,4-bisoxycarbonylbutylene)diphenol

In Examples 7–9, the procedure set fourth in Examples 4–6 was repeated except that 4,4'-(1,4-bisoxycarbonylbutylene)diphenol was substituted for 4,4'[2,2'-oxybis(ethylene-1-oxycarbonyl)]diphenol, in the amounts indicated in Table II below.

EXAMPLES 10–12

Preparation of Polycarbonate From 4,4'-(1,2-bisoxycarbonylethylene)diphenol

In Examples 10–12, the procedure followed in Examples 4–6 was repeated except that 4,4'(1,2-bisoxycarbonylethylene)diphenol was substituted for 4 4'-[2,2'-oxybis(ethylene-1-oxycarbonyl)]diphenol, in the amounts indicated in Table II below.

COMPARATIVE EXAMPLE 13

Preparation of Polycarbonate From Bisphenol A

In this example, polycarbonate was prepared according to the procedure set forth in examples 4–12 above except that the diester bisphenol was omitted.

To measure the oxygen permeabilities of the polycarbonates prepared in the examples above, solutions of the polycarbonates or copolycarbonates (2.0 grams) in methylene chloride (30 milliliters) were filtered through a 0.5 micrometer filter onto glass plates fitted with 4-inch diameter glass casting rings. Solvent was allowed to diffuse from the covered samples for 48 hours, after which the resulting films were dried in a vacuum oven at 40° C. for a minimum of 96 hours. Oxygen permeability measurements were performed on an Oxtran 1000 instrument (Modern Controls, Inc.) and are summarized along with molecular weights and glass transition temperatures, in Table II below.

TABLE II

PROPERTIES OF POLYCARBONATES AND COPOLYCARBONATES

| Example | Composition[a] (%) Diester Bisphenol | Bisphenol A | Mw[b] | Tg (°C.) | PrO2[c] |
|---|---|---|---|---|---|
| 4 | 100 | — | 44,900 | 51 | 6 |
| 5 | 75 | 25 | 46,600 | — | 22 |
| 6 | 50 | 50 | 44,500 | 81 | 49 |
| 7 | 90 | 10 | 53,000 | 70 | 19 |
| 8 | 75 | 25 | 30,000 | — | 44 |
| 9 | 50 | 50 | 37,500 | 72 | 78 |
| 10 | 90 | 10 | 20,100 | — | (d) |
| 11 | 75 | 25 | 19,900 | 90 | (d) |
| 12 | 50 | 50 | 26,900 | 96 | 92 |
| 13 | — | 100 | 54,000 | 145 | 250 |

[a]Mole percent based on total moles of bisphenol present.
[b]Molecular weights are measured by GPC using two linear ultrastyragel columns calibrated against polystyrene standards.
[c]Oxygen permeabilities measured at 25° C., 0% relative humidity, and reported in units of (cm³O₂) (mil)/(100 in²) (24 hour) (atm)
[d]Indicates that the resulting film is too brittle to measure permeability.

As can be seen from the data presented in Table II above, the oxygen permeability properties of the polycarbonates based on the diester bisphenols are much improved over those of the polycarbonate based on bisphenol A. Incorporation of higher levels of diester bisphenol monomer led to a progressive reduction in the oxygen transport rates, with the homopolymer based on the 4,4'-[2,2'-oxybis(ethylene-1-oxycarbonyl)-]diphenol monomer (Example 4) exhibiting the lowest permeability rate reported to date for any aromatic polycarbonate.

Examples 14–16 illustrate the preparation of cyano-substituted bisphenols useful in the present invention.

EXAMPLE 14

Preparation of 5,5-Bis(4-hydroxyphenyl)hexanenitrile

A flask was charged with 5-oxohexanenitrile (23.62 grams, 0.213 mole), phenol (100.0 grams, 1.06 moles), calcium chloride powder (15 grams) and mercaptopropionic acid (1.0 gram). The mixture was heated to 55° C. as gaseous HCl was passed through it for 15 minutes. The resulting orange mixture was maintained at 50°–60° C. until LC analysis showed completion of the reaction (72 hours). The cooled mixture was diluted with ethyl acetate and washed in order with water, saturated sodium bicarbonate solution, water and saturated sodium chloride solution. The mixture was then dried over magnesium sulfate and filtered. Solvent and excess phenol were removed, yielding the cyanobisphenol, 5,5-bis(4-hydroxyphenyl)hexanenitrile, (39.2 grams, 65% yield) as an orange oil.

EXAMPLE 15

Preparation of 4,4-Bis(4-hydroxyphenyl)pentanenitrile

Ethyl 4,4-bis(4-hydroxyphenyl)pentanoate (249.0 grams, 0.792 mole) was stirred with aqueous ammonium hydroxide (29%, 2000 milliliters) at room temperature for 96 hours. The resulting clear brown solution was diluted with water and extracted with ethyl acetate (3×1000 milliliters). The combined organic fractions were then washed with water, saturated sodium bicarbonate solution and then with water, then dried over magnesium sulfate, filtered and concentrated by rotary evaporation. Vacuum drying of the residue gave a tan powder (125.0 grams) which was 95% amide (LC). Reextraction of the ammonium hydroxide fraction (ethyl acetate, 2×1000 milliliters) and workup as before provided an additional 36.0 grams product (71% total yield). Recrystallization from water gave the amide bisphenol, 4,4-bis(4-hydroxyphenyl)pentanamide, as off-white crystals.

A solution of amide bisphenol (120 grams, 0.421 mole) and acetic anhydride (600 milliliters) was next refluxed for 14 hours. The resulting red/orange solution was cooled to room temperature and the volatiles removed under vacuum to leave a viscous orange oil. This oil was refluxed with acetone (500 milliliters) and 10% HCl (100 milliliters) for 1.25 hours. More 10% HCl (100 milliliters) was added and the solution refluxed an additional 3 hours. The cooled solution was then diluted with water and extracted with ethyl acetate (2×600 milliliters). The combined organics were washed with water, saturated sodium bicarbonate solution, again with water, and saturated sodium chloride solution, then dried over magnesium sulfate and filtered and concentrated in vacuo to give a red/orange semisolid. Recrystallization from methanol/water gave the nitrile bisphenol, 4,4-bis(4-hydroxyphenyl)pentanenitrile, as slight yellow crystals (86.5 grams, 77% yield from the amide bisphenol). Colorless crystals were obtained using decolorizing charcoal during recrystallization from methanol/water.

EXAMPLE 16

Preparation of 4,4-bis(4-hydroxy-3-methylphenyl)pentanenitrile

A solution of ethyl 4,4-bis(4-hydroxy-3-methylphenyl)pentanoate (69.00 grams, 0.201 mole) and 29% aqueous ammonium hydroxide (1500 milliliters) was stirred at room temperature for 144 hours. The resulting slightly cloudy, emerald green solution was diluted with water and extracted with ethyl acetate (4×500 milliliters). The combined organic fractions were washed with water, saturated sodium bicarbonate solution and saturated sodium chloride solution. After drying over magnesium sulfate, the solvent was removed in vacuo leaving the amide, 4,4-bis(4-hydroxy-3-methylphenyl)pentanamide, as a tan powder (45.1 grams, 72% yield).

A solution of the amide bisphenol prepared above (45.0 grams, 0.143 mole) and acetic anhdyride (250 milliliters) was then refluxed for 8 hours. Excess acetic anhydride was removed in vacuo to leave a golden orange oil. Crude diacetate was recovered and refluxed with acetone (250 milliliters) and 10% HCl (50 milliliters) for 1.5 hours, at which time an additional 50 milliliters of 10% HCl was added and the reflux continued for 2.5 hours. The cooled reaction solution was diluted with water and extracted with ethyl acetate (2×350 milliliters). The combined organic fractions were washed with water, saturated sodium bicarbonate solution, and saturated sodium chloride solution and then dried over magnesium sulfate and concentrated in vacuo to give 45.0 grams of an orange oil. Flash column chromatography (40% ethyl acetate/hexane, Rf=0.40) gave 24.5 grams (58% yield) of the cyano bisphenol, 4,4-bis(4-hydroxy-3-methylphenyl)pentanenitrile. The nitrile can be recrystallized from toluene/heptane.

Characterization data for the cyano bisphenols obtained in Examples 14–16 are summarized in Table III below.

TABLE III

Example 14: 5,5-Bis(4-hydroxyphenyl)hexanenitrile $^1$H NMR: δ 9.20 (s, 2H), 6.95 (d, 4H, J=8.4 Hz), 6.66 (d, 4H, J=8.4 Hz), 2.43 (m, 2H), 2.06 (m, 2H), 1.49 (s, 3H), 1.21 (m, 2H).

$^{13}$C NMR: δ 155.1, 139.6, 127.9, 120.8, 114.8, 44.0, 40.6, 27.6, 21.0, 16.6.

Example 15: 4,4-Bis(4-hydroxyphenyl)pentanenitrile
MP: 156.0°–157.5° C.

$^1$H NMR: δ 9.22 (s, 2H), 6.95 (d, 4H, J=8.2 Hz), 6.66 (d, 4H, J=8.2 Hz), 2.35 (t, 2H, J=7.3 Hz), 2.14 (t, 2H, J=7.3 Hz), 1.49 (s, 3H).

$^{13}$C NMR: δ 155.3, 138.4, 127.9, 121.0, 114.9, 44.1, 36.9, 26.9, 12.6.

Example 16: 4,4-Bis(y-hydroxy-3-methylphenyl)pentanenitrile
MP: 133.0°–134.5° C.

$^1$H NMR: δ9.09 (s, 2H), 6.84 (s, 2H), 6.77 (d, 2H, J=8.4 Hz), 6.65 (d, 2H, J=8.4 Hz), 2.23 (t, 2H, J=8.1 Hz), 2.12 (t, 2H, J=8.1 Hz), 2.05 (s, 6H), 1.46 (s, 3 Hz).

$^{13}$C NMR: δ153.3, 138.4, 129.9, 125.0, 123.1, 121.1, 114.2, 43.9, 36.9, 26.9, 16.4, 12.6

Examples 17 and 18 illustrate the preparation of polycarbonates from the cyano-substituted bisphenols prepared in Examples 15 and 16 above.

EXAMPLE 17

Preparation of Polycarbonate of 4,4-Bis(4-hydroxyphenyl)pentanenitrile

A flask was charged with 4,4 bis(4-hydroxyphenyl)pentanenitrile prepared in Example 15 (17.36 grams, 0.065 mole), methylene chloride (35 milliliters), water (30 milliliters), 5% triethylamine/methylene chloride solution (1.3 milliliters, 1.0 mole %) and 5% phenol/methylene chloride solution (4.2 milliliters, 3.5 mole %). The pH of the mixture was kept close to 11 by addition of 50% sodium hydroxide solution while phosgene was added over 20 minutes (flow rate=0.4 g/min.). After purging with nitrogen for 15 minutes, the reaction mixture was diluted with methylene chloride, washed with HCl and thereafter repeatedly washed with distilled water. The polymer solution was then dried over magnesium sulfate, filtered and precipitated into methanol. Drying in vacuo at 70° C., 14 hours, left 15.6 grams of fluffy white powder. GPC analysis showed a molecular weight of 92,600.

EXAMPLE 18

Preparation of Polycarbonate of 4,4-Bis-(4-hydroxy-3-methylphenyl)pentanenitrile A flask was charged with 4,4-bis(4-hydroxy-3-methylphenyl)pentanenitrile prepared in Example 16 (11.82 grams, 0.04 mole), methylene chloride (33 milliliters), water (27 milliliters) and 5% triethylamine/methylene chloride solution (1.6 milliliters, 2 mole %). The pH of the mixture was kept close to 11.5–12 by the addition of 50% sodium hydroxide solution while phosgene was added over 20 minutes (flow rate=0.3 g/min.). Between the 5 and 10 minute points of the phosgene addition, a 5% phenylchloroformate/methylene chloride solution (4.5 milliliters, 4 mole %) was added. After purging with nitrogen, the reaction mixture was diluted with methylene chloride, washed with 3% HCl and thereafter repeatedly washed with distilled water. The polymer solution was dried over magnesium sulfate, filtered and precipitated into methanol. Drying in vacuo at 60° C. for 18 hours left 10.21 grams of white solid. GPC analysis showed a molecular weight of 39,000.

Films of each of the polycarbonates prepared above in Examples 17 and 18 were cast from methylene chloride solution or hot pressed, and the glass transition temperatures and oxygen permeabilities for each film obtained.

Oxygen permeability measurements were conducted as described earlier herein, except that solvent was allowed to diffuse from covered samples for 24 hours, after which the resulting films were dried in a vacuum oven at 20° C. below their prior determined glass transition temperature for 24–36 hours.

COMPARATIVE EXAMPLES 19 AND 20

Preparation of Polycarbonates of Bisphenol A and 2,2-Bis(4-hydroxy-3-methylphenyl)propane In comparative Examples 19 and 20, polycarbonate was prepared from conventional bisphenols, i.e., bisphenol A and 2,2-bis(4-hydroxy-3-methylphenyl)propane, respectively.

The data obtained from Examples 17 and 18 and Comparative Examples 19 and 20 are presented in Table IV below.

TABLE IV

| | Properties of Polycarbonates | | |
|---|---|---|---|
| Example | Bisphenol Monomer | Tg (°C.) | PrO$_2$ |
| 17 | 4,4-bis(4-hydroxyphenyl)-pentanenitrile | 150 | 50 |
| 18 | 4,4-bis(4-hydroxy-3-methyl-phenyl)pentanenitrile | 117 | 34 |
| Comp. 19 | Bisphenol A | 145 | 260 |
| Comp. 20 | 2,2-bis(4-hydroxy-3-methyl-phenyl)propane | 98 | 50 |

Glass transition temperatures (Tg) of the cyano-functionalized polymers were higher than those of the unsubstituted analogs and measurements of the oxygen permeability rates for the cyano-substituted polycarbonates showed a dramatic lowering of the transmission rate as compared to the transmission rate of the similar but noncyano-containing polymers.

While the present invention has been described with reference to particular embodiments thereof, it will be understood that numerous modifications may be made by those skilled in the art without actually departing from the spirit and scope of the invention as defined in the appended claims.

What is claimed is:

1. A high molecular weight thermoplastic aromatic polycarbonate resin exhibiting improved oxygen barrier properties, comprising (A) about 50–100 mole percent of structural units of the formula $$-O-\underset{}{\bigcirc}-\overset{O}{\underset{\|}{C}}-O-R_1-O-\overset{O}{\underset{\|}{C}}-\underset{}{\bigcirc}-O-\overset{O}{\underset{\|}{C}}-, \quad (I)$$

(B) any balance being structural units of the formula

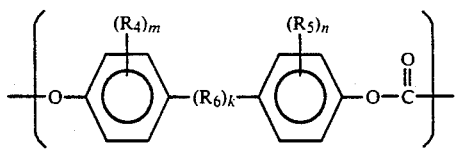 (II)

wherein $R_1$ is a divalent aliphatic hydrocarbon radical, divalent aromatic radical or divalent aliphatic ether radical; $R_4$ and $R_5$ are independently monovalent hydrocarbon radicals or halogen radicals; $R_6$ is a divalent hydrocarbon radical or a

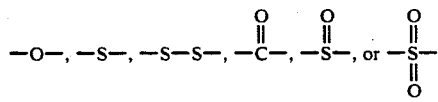

radical; m and n are independently numbers in the range of 0 to about 4; and k is 0 or 1.

2. The polycarbonate of claim 1 comprising units of formula (I) wherein $R_1$ is a divalent alkylene, cycloalkylene, alkylene ether, or cycloalkylene ether group.

3. The polycarbonate of claim 2 wherein $R_1$ is a branched or straight chain divalent alkylene group containing about 1 to about 20 carbon atoms, or a divalent cycloalkylene group containing about 4 to about 7 ring carbon atoms.

4. The polycarbonate of claim 3 wherein $R_1$ is a straight chain divalent ethylene or butylene group.

5. The polycarbonate of claim 2 wherein $R_1$ has the general formula:

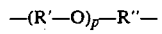

wherein R' and R" are independently branched or straight chain alkylene groups containing about 1 to about 20 carbon atoms or cycloalkylene groups containing about 4 to about 7 ring carbon atoms, and p is a positive number in the range of about 1 to about 10.

6. The polycarbonate of claim 5 wherein R' and R" are both straight chain ethylene groups and p is 1.

7. The polycarbonate of claim 1 comprising units of formula (II) wherein $R_2$ and $R_3$ are alkyl radicals having 1 to about 10 carbon atoms, and m and n are 1.

8. The polycarbonate of claim 7 wherein $R_2$ and $R_3$ are methyl groups.

9. The polycarbonate composition of claim 8 wherein $R_2$ and $R_3$ are methyl groups at the 3,3' positions of the aromatic rings with respect to X.

10. The polycarbonate of claim 1 comprising units of formula (II) wherein m and n are 0.

11. The polycarbonate of claim 1 wherein $R_4$ and $R_5$ are independently alkyl, cycloalkyl, aryl, arylalkyl or alkylaryl groups, and $R_6$ is an alkylene, cycloalkylene, alkylidene or cycloalkylidene group.

12. The polycarbonate of claim 11 wherein $R_4$ and $R_5$ are independently alkyl groups containing about 1 to about 10 carbon atoms, cycloalkyl groups containing about 4 to about 7 ring carbon atoms, aryl groups containing about 6 to about 12 ring carbon atoms, or arylalkyl or alkylaryl groups containing about 7 to about 14 carbon atoms, and $R_6$ is an alkylene or alkylidene group containing about 1 to about 10 carbon atoms or cycloalkylene or cycloalkylidene groups containing about 4 to about 7 ring carbon atoms, m and n in Formula (III) are 1, and k is 1.

13. The polycarbonate of claim 12 wherein $R_4$ and $R_5$ are methyl groups, and $R_6$ is an isopropylidene group.

14. The polycarbonate composition of claim 13 wherein $R_4$ and $R_5$ are methyl groups in the 3,3' positions of the aromatic rings with respect to $R_6$.

15. The polycarbonate of claim 14 wherein m and n in Formula (III) are 0.

16. The polycarbonate of claim 1 comprising structural units of formula (I) in an amount ranging from about 65 to about 2100 mole percent based on total structural units.

* * * * *